US00PP37505P2

(12) United States Plant Patent
Nannes

(10) Patent No.: US PP37,505 P2
(45) Date of Patent: Jun. 30, 2026

(54) ***ECHEVERIA* PLANT NAMED 'BINL-77120302'**

(50) Latin Name: *Echeveria spp.*
Varietal Denomination: BINL-77120302

(71) Applicant: Botanical Innovation B.V., Wageningen (NL)

(72) Inventor: Jacobus A. M. Nannes, Nairobi (KE)

(73) Assignee: Botanical Innovation (NL)

( * ) Notice: Subject to any disclaimer, the term of this patent is extended or adjusted under 35 U.S.C. 154(b) by 0 days.

(21) Appl. No.: 19/344,906

(22) Filed: Sep. 30, 2025

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
CPC ..... A01H 5/12; A01H 5/00; A01H 6/32
See application file for complete search history.

*Primary Examiner* — June Hwu

(57) ABSTRACT

A new and distinct cultivar of *Echeveria* plant named 'BINL-77120302' is disclosed, characterized by intense red color of the distal leaf surface of the older leaves and fully red young leaves in the heart/center of the plant. Foliage is thick and evenly spaced, forming a flattened rosette plant shape. The new cultivar is an *Echeveria*, typically used as an ornamental plant.

2 Drawing Sheets

Figure 1:
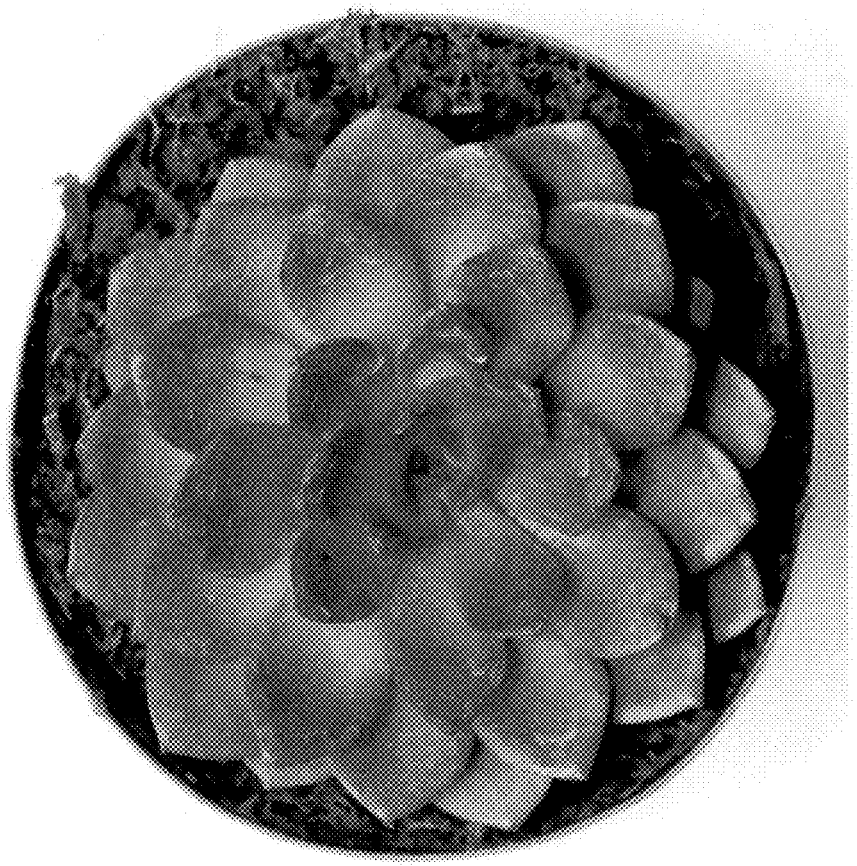

Latin name of the genus and species: *Echeveria spp.*
Cultivar denomination: 'BINL-77120302'.

BACKGROUND OF THE INVENTION

The new cultivar is a product of a planned breeding program to produce distinct and better performing *Echeveria* cultivars. The new cultivar is the result of a crossing made by the inventor in May of 2019. The seed parent is the unpatented *Echeveria* 'Red Edge'. The pollen parent is the unpatented *Echeveria* 'Nina'. The new cultivar was selected by the inventor in August of 2020 at a nursery in Nairobi, Kenya.

Asexual reproduction of the new cultivar 'BINL-77120302' by terminal cuttings was first performed at the same nursery in Nairobi, Kenya in August of 2020, and has shown that the unique features of this cultivar are stable and reproduced true to type through successive generations.

SUMMARY OF THE INVENTION

The cultivar 'BINL-77120302' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77120302'. These characteristics in combination distinguish 'BINL-77120302' as a new and distinct *Echeveria* cultivar:

1. Intense red color of the distal leaf surface of the older leaves and fully red young leaves in the heart/center of the rosette-like plant.
2. Thick leaves, hence not stretching easily or quickly.
3. Ornamental, evenly spaced foliage forming a flattened rosette plant-shape.

PARENT COMPARISONS

Plants of the new cultivar 'BINL-77120302' are similar to plants of the female parent in most horticultural characteristics, however, plants of the new cultivar 'BINL-77120302' differ from in the following characteristics:

1. Leaf color of the new cultivar is red on the distal leaf surface of the older leaves and more full red young leaves in the heart/center of the rosette-like plant. Leaf color of the seed parent is green with a small/narrow red leaf-rim/edge.
2. Plants of the new cultivar have a less upright growth habit than plants of the seed parent.

Plants of the new cultivar 'BINL-77120302' are similar to plants of the male parent in most horticultural characteristics, however, plants of the new cultivar 'BINL-77120302' differ in the following characteristics:

1. Leaf color of the new cultivar is red on the distal leaf surface of the older leaves and more full red young leaves in the heart/center of the rosette-like plant. Leaf color of the pollen parent is more evenly colored, with younger leaves fully pinkish-red, older leaves turn to a more red-green color.
2. Leaves of the new cultivar are less pointed to the leaf end than leaves of the pollen parent.

COMMERCIAL COMPARISONS

Plants of the new cultivar 'BINL-77120302' are similar to plants of the commercial cultivar *Echeveria* 'Mont', unpatented. However, plants of the new cultivar differ in the following characteristics:

1. Leaf color of the new cultivar is red on the distal leaf surface of the older leaves. In the center of the plant there are more entirely red young leaves. Leaf color of this comparator is more evenly colored, with younger leaves fully pinkish-green-red, older leaves turn to a more dull green color.
2. Leaves of the new cultivar are less round than leaves of this comparator.

Plants of the new cultivar 'BINL-77120302' are similar to plants of the commercial cultivar *Echeveria* 'Spotlight', unpatented. However, plants of the new cultivar differ in the following characteristics:

1. Leaf color of the new cultivar is red on the distal leaf surface of the older leaves and young foliage is entirely red in the heart/center of the rosette-like plant. Leaf color of this comparator is evenly green colored with red leaf-tips.
2. Plants of the new cultivar have less upright habits than plants of this comparator.

BRIEF DESCRIPTION OF THE PHOTOGRAPHS

The accompanying photograph in FIG. 1 illustrates in full color a top-down view of a typical plant of 'BINL-77120302' grown in a greenhouse. The plant is approximately 24 weeks of age in a 12 cm pot.

Figure 2:
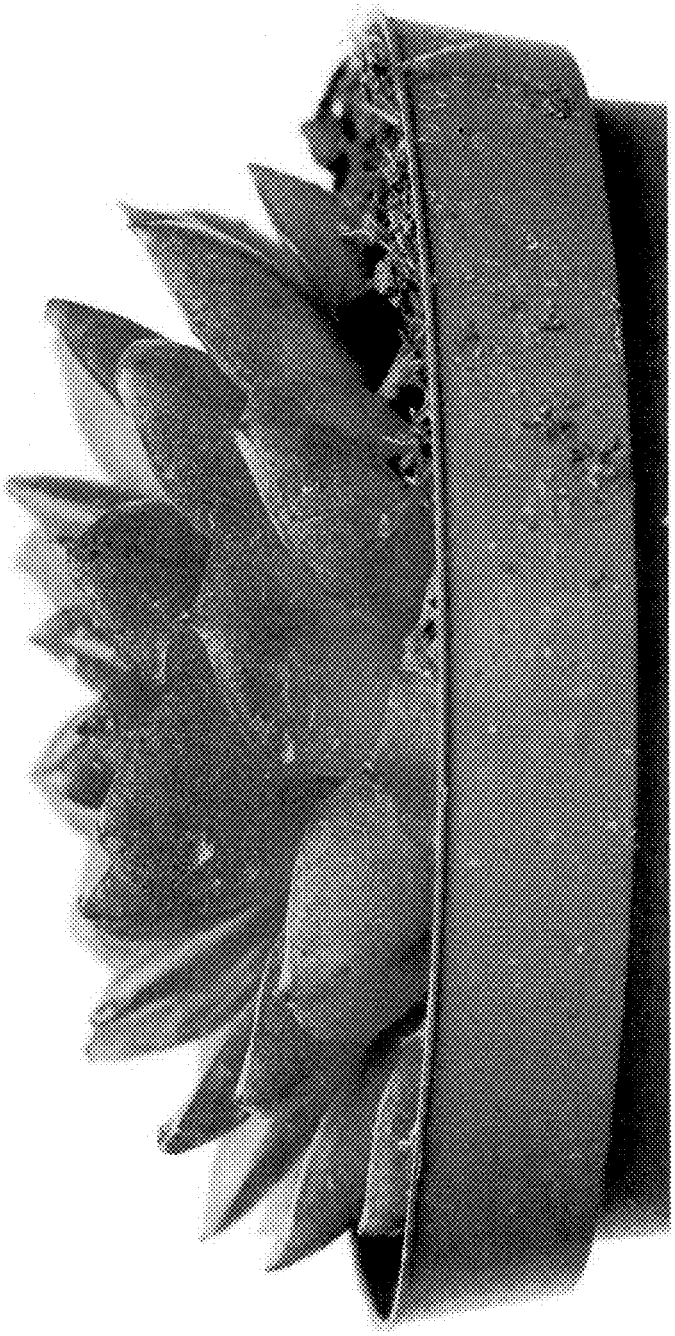

FIG. 2 is a side-view of the same plant.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-77120302' plants at 24 weeks of age, grown in a greenhouse in Nairobi, Kenya during August. The growing temperature ranged from 12° C. to 20° C. at night to 20° C. to 28° C. during the day. Measurements and numerical values represent averages of typical flowering types.

Botanical classification: *Echeveria* spp. 'BINL-77120302'.

PROPAGATION

Time to initiate roots: About 14 days in summer, 21 days in winter at approximately 20° C.

Time to produce rooted cutting: About 45 days in summer, 60 days in winter at approximately 20° C.

Description of roots: Thin, herbaceous, moderately dense, freely branching. White in color, not accurately measured with R.H.S. chart.

PLANT

Plant type: Tender succulent perennial.

Plant shape: Flattened (basal rosette).

Growth habit: Basal rosette of leaves.

Plant spread: Average 11.9 cm.

Height: Average 5.2 cm.

Age of plant described: Approximately 24 weeks.

Branching habit: Leaves in basal rosettes, no main stems or lateral stems present.

Pinching: Pinching not required.

FOLIAGE

Leaf:

*Arrangement*.—Single rosette.

*Quantity*.—Average 40 per rosette.

*Average length*.—4.8 cm.

*Average width*.—1.6 cm.

*Shape*.—Obovate.

*Aspect*.—Very slightly concave, leaves in an average angle of 20° to horizontal (=0°).

*Apex*.—Abruptly acute.

*Base*.—Cuneate.

*Margin*.—Entire.

*Texture*.—Top surface: Glabrous, smooth. Bottom surface: Glabrous, smooth.

*Pubescence*.—None; both sides glabrous.

*Luster, upper side*.—Moderately glossy.

*Luster, under side*.—Moderately glossy.

*Rugosity, upper side*.—Non-rugose.

*Rugosity, under side*.—Non-rugose.

*Color*.—Young foliage upper side: RHS Greyed-Purple N186C, narrowly margined 187A, fading to Greyed-Orange 177C towards the base, narrowly margined Greyed-Purple 184B and 184C. Young foliage under side: RHS Greyed-Purple 187A, narrowly margined Greyed-Purple 187C, fading to Greyed-Red 182B and Greyed-Purple 183D towards the base, narrowly edged Greyed-Purple 185B. Mature foliage upper side: RHS Yellow-Green 147C, upper ¼ Greyed-Purple N186C and a blend of Greyed-Purple N186C to Brown 200B, and narrowly edged a blend of Greyed-Purple N186C to Brown 200B and Greyed-Purple 187B towards the base. Mature foliage under side: RHS Yellow-Green 147C, upper ¼ Greyed-Purple N186C, narrowly edged Greyed-Purple N186C margins of lower ¾ narrowly edged Brown 200D, Greyed-Purple 184B towards the base.

*Venation*.—Pattern: No veins visible. Mature leaf venation color, under side: No veins visible, except for main vein on under side, colored RHS Brown 200B and 200C.

*Other*.—Leaves succulent, average thickness: 8 mm.

OTHER CHARACTERISTICS

Flower: Not observed to date.

Seeds and fruits: None observed to date.

Disease/pest resistance: Neither resistance nor susceptibility to normal diseases and pests of *Echeveria* have been observed.

Temperature tolerance: Tolerates temperatures up to 40° C. Hardy to USDA zones 11 to 13. Moderate tolerance to rain. High tolerance to wind.

What is claimed is:

1. A new and distinct cultivar of *Echeveria* plant named 'BINL-77120302' as herein illustrated and described.

* * * * *